United States Patent [19]

Nakagawa et al.

[11] Patent Number: 5,460,658
[45] Date of Patent: Oct. 24, 1995

[54] METHOD FOR CLEANING OR PRESERVING A CONTACT LENS BY MEANS OF LIQUID COMPOSITION

[75] Inventors: Akira Nakagawa; Kaoru Kamiya, both of Nagoya, Japan

[73] Assignee: Tomei Sangyo Kabushiki Kaisha, Nagoya, Japan

[21] Appl. No.: 261,869

[22] Filed: Jun. 17, 1994

Related U.S. Application Data

[60] Continuation of Ser. No. 994,324, Dec. 21, 1992, abandoned, which is a division of Ser. No. 706,200, May 28, 1991, abandoned.

[30] Foreign Application Priority Data

Jun. 18, 1990 [JP] Japan .......................... 159460

[51] Int. Cl.⁶ .......................... C11D 3/386; B08B 3/04
[52] U.S. Cl. .......................... 134/42; 252/106; 252/139; 252/174.12
[58] Field of Search .......................... 134/42; 252/106, 252/174.12, DIG. 12, 139; 435/188

[56] References Cited

U.S. PATENT DOCUMENTS

| | | | |
|---|---|---|---|
| B 458,819 | 4/1976 | Weber | 252/545 |
| 4,096,870 | 6/1978 | Manfuso, Jr. | 134/28 |
| 4,462,422 | 7/1984 | Boskamp | 252/174.12 |
| 4,500,441 | 2/1985 | Tanaka et al. | 252/89.1 |
| 4,690,773 | 9/1987 | Ogunbiyi et al. | 252/174.12 |
| 4,710,313 | 12/1987 | Miyajima et al. | 252/105 |
| 4,738,790 | 4/1988 | Miyajima et al. | 252/105 |
| 4,959,179 | 9/1990 | Aronson et al. | 252/135 |
| 5,039,446 | 8/1991 | Estell | 252/174.12 |
| 5,145,643 | 9/1992 | Dziabo et al. | 422/28 |
| 5,145,644 | 9/1992 | Park et al. | 422/28 |
| 5,281,277 | 1/1994 | Nakagawa et al. | 134/18 |
| 5,314,823 | 5/1994 | Nakagawa | 435/264 |

FOREIGN PATENT DOCUMENTS

| | | |
|---|---|---|
| 0080748 | 6/1983 | European Pat. Off. . |
| 177183 | 4/1986 | European Pat. Off. . |
| 1-180515 | 7/1989 | Japan . |
| 2-168224 | 6/1990 | Japan . |
| 5-77047 | 10/1993 | Japan . |
| 2178054 | 2/1987 | United Kingdom ........ 252/DIG. 12 |

OTHER PUBLICATIONS

Patent Abstracts of Japan, vol. 71, No. 47 (c–173), Jun. 28, 1983 & JP–A–58–059909, Apr. 9, 1983, A. Taizou, "Bath Liquid Composition".

Patent Abstracts of Japan, vol. 134, No. 64 (p–947), Oct. 20, 1989 & JP–A–11–80515, Jul. 18, 1989, N. Megumi et al, "Cleaning Liquid and Cleaning Method for Contact Lens".

*Primary Examiner*—Jan H. Silbaugh
*Assistant Examiner*—Saeed Chaudhry
*Attorney, Agent, or Firm*—Oblon, Spivak, McClelland, Maier & Neustadt

[57] ABSTRACT

A liquid composition for contact lenses, which comprises from 0.01 to 5% (W/V) of a protease, from 5 to 30% (W/V) of a polyhydric alcohol, from 1 to 5% (W/V) of an alkali metal salt and from 0.5 to 20% (W/V) of a surfactant.

13 Claims, No Drawings

METHOD FOR CLEANING OR PRESERVING A CONTACT LENS BY MEANS OF LIQUID COMPOSITION

This application is a Continuation of application Ser. No. 07/994,324, filed on Dec. 21, 1992, now abandoned, which is a divisional of application Ser. No. 07/706,200, filed May 28, 1991, now abandoned.

The present invention relates to a liquid composition for contact lenses and a method for cleaning or preserving a contact lens by means of such a liquid composition. More particularly, it relates to a liquid composition which is capable of effectively removing soil such as protein soil or lipid soil deposited on a contact lens and which is at the same time useful as a preserving solution for a contact lens, and a method of cleaning or preserving a contact lens by means of such a liquid composition.

When contact lenses are put on the eyes, soils such as lipids derived from e.g. sebum or proteins derived from the lacrimal components tend to deposit thereon. Therefore, when taken off from the eyes, such contact lenses must be cleaned to remove such soils.

With respect to lipid soil among such soils, it has been common to remove it by rubbing and washing by means of a cleaning solution containing a surfactant. After this washing, the contact lenses are rinsed with running water and then soaked and preserved in a prescribed preserving solution to store them in a sanitary condition. In recent years, a cleaning-preserving solution which serves as both a preserving solution and a washing solution to remove lipid soil, has been developed and commonly used.

On the other hand, protein soil can not be removed by a surfactant. Therefore, users of contact lenses have to conduct cleaning and removal of such protein soil separately. As a cleaning agent for removing this protein soil, a cleaning agent containing a protease has been presented in recent years. However, the protease is usually unstable in a dilute solution state in which it exhibits its activity, and it gradually loses its activity. Therefore, the cleaning agent containing such a protease is usually supplied in a stable solid formulation such as a tablet, a granule or a powder, so that the users may use it by dissolving it in purified water or a prescribed dissolving solution such as a solution containing a surfactant, as the case requires.

Namely, heretofore, for the maintenance of contact lenses, the uses of such contact lenses had to have an enzyme formulation to remove protein soil, a dissolving solution to dissolve such as enzyme formulation and a cleaning-preserving solution (or a cleaning solution and a preserving solution) to store the contact lenses. After removal of the contact lenses, the cleaning solution (or a cleaning-preserving solution) containing a surfactant is dropped thereto and the lenses are rubbed with fingers to remove lipid soil. Then, the enzyme formulation is dissolved in the dissolving solution, and the contact lenses are soaked therein for a predetermined period of time to remove proteins. After completion of such treatment, the lenses have to be transferred to a separately prepared preserving solution (or a cleaning-preserving solution). Thus, the maintenance of contact lenses used to be very cumbersome.

Under these circumstances, Japanese Examined Patent Publication No. 59123/1988 proposes a cleaning agent which is a solid formulation containing an enzyme and a surfactant together with a foaming agent and a foaming assistant and which is to be put into purified water for use in the form of a solution. However, also in this case, it was cumbersome to dissolve the solid formulation each time.

Therefore, it is desired to preliminarily incorporate a protease in a solution state to a cleaning-preserving solution containing a surfactant, thereby to obtain a cleaning-preserving solution so that removal of proteins, cleaning of lipids and preservation can be conducted in a single solution. However, since the protease is extremely unstable in a dilute solution, it has been considered difficult to provide it in the form of a solution.

On the other hand, in the field of cleaning agents, foods, etc., some methods have been proposed to stabilize an enzyme in a solution by an addition of a stabilizer (Japanese Examined Patent Publications No. 152/1966 and No. 131386/1981). However, in these methods, it is a prerequisite to use such an enzyme solution by diluting it with e.g. water, and the enzymatic activity can not be obtained by the solution by itself. Further, ethanol or the like used there as the stabilizer will adversely affect lens materials and therefore can not be used for contact lenses.

Further, as a cleaning solution for contact lenses, Japanese Unexamined Patent publication No. 159822/1988 or No. 180515/1989 proposes a method of stabilizing a protease by incorporating the protease to a solution containing at least 50% of an organic liquid miscible with water. However, the enzymatic activity obtained by this solution was extremely low, and the cleaning effects were not practically adequate.

Further, Japanese Unexamined Patent Publication No. 167726/1989 discloses a preserving solution having an enzyme incorporated together with a water-soluble polymer compound containing quaternary ammonium groups and hydroxyl groups. However, also in this case, the cleaning effects were low, and the product was not adequate as a cleaning agent.

The present invention has been accomplished under these circumstances. It is an object of the present invention to provide a liquid composition whereby a , protease may be stabilized in a solution state for a long period of time and which is capable of providing adequate enzymatic activities to clean the contact lenses. It is a further object of the present invention to make it possible to conduct the maintenance of contact lenses easily and effectively by means of such a liquid composition.

In order to solve the above problems, the present inventors have conducted extensive researches to find an enzyme stabilizer capable of inducing an enzymatic activity sufficient for cleaning without adversely affecting the lens material for contact lenses. As a result, the present invention has been accomplished.

Thus, the present invention provides a liquid composition for contact lenses, which comprises from 0.01 to 5% (W/V) of a protease, from 5 to 30% (W/V) of a polyhydric alcohol, from 1 to 5% (W/V) of an alkali metal salt and from 0.5 to 20% (W/V) of a surfactant. Here, "% (W/V)" represents the amount (weight) of each component by percentage in 100 parts by volume of the liquid composition.

Further, in the present invention, such a liquid composition for contact lenses may advantageously further contain not more than 2% (W/V) of nitrilotriacetic acid or its salt, or an α-oxycarboxylic acid or its salt.

The present invention also provides a method for cleaning a contact lens, which comprises contacting the contact lens to such a liquid composition to remove a soil such as protein soil or lipid soil deposited on the contact lens.

Further, the present invention provides a method for preserving a contact lens, which comprises soaking the contact lens in such a liquid composition.

Now, the present invention will be described in detail with reference to the preferred embodiments.

Proteases are generally classified into four kinds i.e. serine protease, thiol protease, metal protease and carboxyl protease, depending upon the respective active sites. Among them, the serine protease is preferably employed in the present invention.

As the thiol protease, an enzyme derived from a plant, such as papain or blomelain, a protease of Genus Clostridium as bacteria (clostripain) or a protease of baker's yeast, is known, but these proteases have thiol groups as their active catalytic sites and thus require a reducing agent such as cysteine or thiourea. Such a reducing agent is apt to oxidation by oxygen in the atmosphere, and it is thereby difficult to maintain it in a liquid formulation in a stabilized state. As the metal protease, collagenase or a neutral protease of Genus Bacillus as bacteria, is known. But, it has a metal such as zinc as its active catalytic site, and it is known that it loses its activity by a metal chelating agent. In the present invention, a metal chelating agent may possibly be incorporated as an optional blend component. Therefore, the enzyme of this type may not be suitable in some cases. The carboxyl protease is an enzyme generally called an acidic protease and has an activity in an acidic region. For a solution which is highly likely to be in contact with fingers or eyes such as the solution for contact lenses, it is not desirable that its pH is brought to a highly irritative acidic region.

Whereas, the serine protease requires no reducing agent, is not influenced by a metal chelating agent and has an optimum pH for enzymatic activity from neutral toward an alkaline side. Thus, it is suitable for use in the present invention. Such a serine protease is an enzyme with its active catalytic sites concerned with serine residues, and it is known that such a serine protease is deactivated by a reagent such as diisopropylfluorophosphoric acid or phenylmethanesulfonylfluoride which specifically bonds to serine residues. Depending upon the inactivation mode against such a reagent, a substance is determined as to whether or not it is a serine protease.

Specific examples of the serine protease include, for example, trypsin and chymotripsin derived from animals, Streptomyces protease derived from actinomycetes, Bacillus protease derived from bacteria and Aspergillus protease derived from mold. Further, various types of such protease are commercially available, including, for example, "Bioprase" (manufactured by Nagase Seikagaku Kogyo K. K.), "Alcarase", "Esperase", "Sabinase", "Subtilisin A", "PEM" (manufactured by Novo Nordisk Bioindustry Ltd.), "Protease N AMANO" "Protease P AMANO" (manufactured by Amano Pharmaceutical Co., Ltd.) and "Actinase" (manufactured by Kaken Pharmaceutical Co., Ltd.). For practical use, a suitable protease will be selected among them. Among the commercial products, there are some in which a protease other than the serine protease, or a carbohydrolytic enzyme or a lipolytic enzyme such as amylase or lipase, may inevitably be included during the process for their purification.

In the present invention, the amount of the protease to be incorporated, is determined suitably depending upon the desired cleaning effects and the period of its use. Namely, it is usually considered that the larger the amount of the protease used, the higher the cleaning effects. However, in the case of a soil deposited on a lens surface, the amount of the enzyme capable of acting on the soil is practically limited, and even if the protease is added beyond a certain level, no further improvement in the cleaning effects will be obtained. Further, at a high concentration, not only no further improvement in the cleaning effects will be obtained, but also there will be a possible danger of damaging the skin during the cleaning operation. On the other hand, if the amount of the protease is too small, no adequate cleaning effects will be obtained, and even with a stabilized enzyme, if left to stand at a high temperature for a long period of time, the enzymatic activities tend to drop to some extent. Accordingly, the amount of the protease to be incorporated is selected within a range such that even if the enzymatic activities will drop to some extent during the intended period of use, the cleaning effects will not drop. In this respect, in the present invention, the amount of the protease is determined to bring the concentration at a level of from 0.01 to 5% (W/V).

Further, in the present invention, the polyhydric alcohol and the alkali metal salt are incorporated in combination as the components to stabilize the protease in the solution. Needless to say, these materials must be ones which are highly safe to vital tissues and which do not adversely affect the contact lens material.

Specific examples of such a polyhydric alcohol include, for example, glycerol, sorbitol, mannitol, erythritol, dulcitol and inositol. Among them, one or more will be selected for use. These polyhydric alcohols are preferred for the present invention, since they have a high activity for stabilizing the enzyme and a low activity for weakening the enzymatic effects of the protease.

The amount of such a polyhydric alcohol is suitably selected within a range of from 5 to 30% (W/V) depending upon e.g. the desired cleaning effects and the stability of the enzyme. If the amount is less than the above range, no adequate effects for stabilizing the enzyme will be obtained. On the other hand, if the amount exceeds the above range, the enzymatic effects of the protease tends to be low.

On the other hand, the alkali metal salt is generally known to increase the ion strength of the solution and contribute to stabilization of the enzyme, but such effects are not so high. However, as a result of the research by the present inventors, it has been found that when it is used in combination with the above-mentioned polyhydric alcohol, the activity for stabilizing the enzyme can be further improved. Further, heretofore, a component capable of stabilizing an enzyme has been considered to decrease the enzymatic activities of the protease. However, it has been unexpected found that the alkali metal salt does not hinder the enzymatic activities and gives no adverse effects to the soil removal of the lenses.

As such an alkali metal salt, a sodium salt, a potassium or a lithium salt may be mentioned. More specifically, sodium chloride, potassium chloride or lithium chloride may be employed. In the present invention, sodium chloride is used particularly preferably. It is incorporated in an amount of from 1 to 5% (W/V). If the amount is less than 1% (W/V), no adequate effects will be obtained. On the other hand, if it is incorporated beyond 5% (W/V), no further effects can be expected.

Further, in the present invention, it is preferred to add a borate, particularly an alkali metal salt of boric acid readily soluble in water, such as sodium borate, potassium borate or sodium tetraborate (borax) in an amount of not higher than about 0.5% (W/V), in order to further improve the stability of the protease. The mechanism for stabilizing the enzyme by this borate has not yet been clearly understood. However, it is possible that such a borate forms a complex compound together with the protease and a polyhydric alcohol, whereby the three dimensional structure of the protease is stabilized. If its amount is too small, no adequate effects as boric acid for stabilizing the protease will be obtained.

Therefore, in order to obtain the effects for stabilization, the borate is preferably incorporated in an amount of at least 0.05% (W/V).

Among proteases, there are some which have, in their molecules, sites linkable with calcium ions and which take more stabilized molecular structures as they take calcium ions in their molecules. When such proteases are used, it is advisable to further improve their stability by adding calcium ions in an amount of not higher than about 0.01% (W/V). As a source for supplying such calcium ions, calcium chloride, calcium nitrate or calcium acetate is, for example, preferred which has excellent solubility in water. In addition to the above protease and the above polyhydric alcohol and the above alkali metal salt as the components for stabilizing the protease, the liquid composition of the present invention contains a surfactant as a component for removing lipid soil deposited on contact lenses. The type of the surfactant is not particularly limited. However, from the viewpoint of cleaning power, nonionic and anionic surfactants are preferred. Anionic surfactants have high lipid cleaning effects and excellent lubricating properties, but they are generally known to have strong irritation to the skin and to adversely affect against the stability of the protease. Whereas, nonionic surfactants are weak in the irritation to the skin and give no adverse effects to the stability of the protease, and further have a function to control the above-mentioned drawbacks of the anionic surfactants, although their cleaning power is lower than the anionic surfactants. Accordingly, in the present invention, it is preferred to employ a nonionic surfactant, or a combination of a nonionic surfactant and an anionic surfactant.

More specifically, the nonionic surfactants include, for example, a polyethylene glycol adduct of a higher alkylamine, a polyethylene glycol adduct of a higher fatty acid amide, a polyglycerol ester of a higher fatty acid, a polyalkylene glycol of a higher fatty acid, a polyethylene glycol copolymer ester, a polyethylene glycol ether of a higher alcohol, a polyglycerol ether of a higher alcohol, a formaldehyde condensation product of polyethylene glycol of an alkylphenol, a polypropylene glycol-polyethylene glycol copolymer and a polyethylenesorbitan alkyl ester.

On the other hand, specific examples of the anionic surfactants include a sodium alkylsulfate, a sodium alkylbenzene sulfonate, a sodium alkyloylmethyl taurine, a sodium alkyloylsarcosine, a sodium a-olefinsulfonate, a sodium polyoxyethylenealkyl ether sulfate and a sodium polyoxyethylenealkylphenol ether sulfate.

Among these surfactants, one or more will suitably be selected taking into consideration the desired cleaning effects and the stability of the enzyme. As mentioned above, the higher the proportion of the anionic surfactant, the higher the lipid cleaning power, but the lower the stability of the enzyme. On the other hand, the higher the proportion of the nonionic surfactant, the higher the stability of the enzyme, but the lower the lipid cleaning power. Therefore, the mixing ratio of the nonionic surfactant to the anionic surfactant can not generally be defined, but is usually preferably within a range of from 100:0 to 20:80 by weight. Further, the overall proportion of the surfactant is preferably within a range of from 0.5 to 20% (W/V). If the surfactant is less than this range, the effects for cleaning lipid soil tend to be low. On the other hand, if the amount exceeds this range, no further improvement in the cleaning effects will be obtained.

In a case where a solution containing a protease is applied to contact lenses, the protein of such a protease is likely to be adsorbed in the same manner as lacrimal proteins are adsorbed on the contact lens. If such a protein of a protease is adsorbed and remains on a contact lens, there will be a possible danger that such a protein becomes an allergen or causes ophthalmopathy. However, according to the present invention, this problem can also be prevented from occurring. Namely, the mechanism of adsorption of a protein to a lens is complicated and is believed to be due to an ionic bonding force or a hydrophobic bonding force. With the liquid composition of the present invention, adsorption of a protein to such a lens surface can effectively be prevented by the action of the above-mentioned surfactant and the above-mentioned alkali metal salt.

In fact, when a protease or lacrimal proteins are dissolved in purified water or in a buffer solution, and a contact lens is soaked in the solution, such proteins are adsorbed on the contact-lens surface, whereby the hydrophilic nature of the lens surface changes, and it is observed that wettability with water increases. Whereas, even if a protease or lacrimal proteins are dissolved in the liquid composition of the present invention and a contact lens is soaked in the solution, no change is observed in the wettability with water of the lens surface, and no adsorption of the proteins to the lens is observed. Accordingly, if a contact lens is cleaned or preserved by means of such a liquid composition, the protein of the protease will not remain on the lens surface, and adsorption of lacrimal proteins can be prevented, whereby there will be no danger of causing the above-mentioned ophthalmopathy.

Thus, with the liquid composition comprising a protease, a polyhydric alcohol, an alkali metal salt and a surfactant in the respectively prescribed amounts, it is possible to maintain the protease in a solution state under a stabilized condition for a long period of time without reducing the cleaning effects of the protease, by the functions of the polyhydric alcohol and the alkali metal salt, whereby the effects for the removal of protein soil deposited on a contact lens are high. Further, such a liquid composition contains also a surfactant, whereby lipid soil on the contact lens can also be removed. Thus, it is possible to remove the protein soil and the lipid soil in a single solution, and the solution can also be used as a preserving solution for contact lenses. Accordingly, the cleaning and preservation of contact lenses can be conducted very easily and efficiently.

Further, to the liquid composition for contact lenses of the present invention, commonly employed antiseptics, viscosity builders, buffering agents, metal chelating agents, etc. may further be incorporated as the case requires.

For example, the antiseptics are added to prevent propagation of fungi during the storage. Specifically, they include, for example, potassium sorbate, sodium sorbate, sodium salicylate, sodium benzoate, and a methyl ester, an ethyl ester, a propyl ester and a butyl ester of p-oxybenzoic acid. Such an antiseptic is incorporated usually in an amount of not higher than 1% (W/V).

The viscosity builders are added to facilitate cleaning with fingers. Specifically, they include, carboxymethyl cellulose, carboxypropyl cellulose, hydroxyethyl cellulose, hydroxypropyl cellulose, hydroxypropylmethyl cellulose, a copolymer of isobutylene with maleic anhydride, polyvinyl alcohol, sodium alginate, karagynan, starch and gum arabic. Such a viscosity builder is incorporated usually in an amount of not higher than 2% (W/V).

The buffering agents are added to minimize the irritation to the eyes or to maintain the pH at a level where the protease is stable. For example, a phosphoric acid type, triethanolamine-hydrochloric acid or acetic acid type, or tris(hydroxymethyl)aminomethanehydrochloric acid type buffering agent may be used. Such a buffering agent is incorporated usually in an amount of not higher than 10% (W/V) to maintain the pH at a level from 5 to 10, preferably from 6 to 9.

The metal chelating agents are added to prevent adhesion of an inorganic substance to contact lenses or to remove an inorganic substance deposited on the lens surface. For example, ethylenediamine tetraacetic acid, nitrilotriacetic acid, an α-oxycarboxylic acid such as citric acid, gluconic acid or tartaric acid, or a sodium salt thereof, and a condensed phosphoric acid salt such as sodium hexametaphosphate or sodium tetraphosphate, may be used. However, as mentioned above, among the proteases, there are some which will be stabilized in a state where calcium is taken into the molecule. On the other hand, among the metal chelating agents, there are some which take in also calcium present in the enzyme molecule. Particularly, among those mentioned above, ethylenediamine tetraacetic acid and its sodium salt have strong chelating activities, and they may adversely affect the stability of the enzyme. Further, the condensed phosphate does not have adequate effects for removing an inorganic substance deposited on the contact lens surface.

Under these circumstances, the present inventors have conducted an extensive research and, as a result, have found that nitrilotriacetic acid, α-oxycarboxylic acid and their salts are effective to prevent deposition of inorganic substances on the lens surface and to remove inorganic substances deposited on the lens, without adversely affecting the stability of the enzyme. Accordingly, in the present invention, the metal chelating agent is preferably selected from the group consisting of nitrilotriacetic acid, α-oxycarboxylic acid and their salts. Such a chelating agent is incorporated preferably in an amount of not exceeding 2% (W/V).

The liquid composition of the present invention may be presented in the form of one-pack system by dissolving all of the above described components in a solvent such as purified water. However, it is also possible to present it in the form of a two-pack system so that the protease can be maintained in a further stabilized condition, or one of them may, of course, be supplied in a solid form such as tablets, granules or powder. In the case of two-pack system, it is preferred that the protease is supplied in a concentrated form together with an enzyme stabilizer component and will be diluted with a separately prepared liquid agent containing other components such as a surfactant. However, the enzyme stabilizer component may not necessarily be incorporated together with the protease, and it may be suitably distributed to both of the two liquids depending upon the capacity of supply. In a case where one of them is supplied in a solid form, it is preferred that the protease is also in a solid form and mixed together with a solid stabilizer component, and the mixture is formed into a formulation of tablet, granule or powder. In use, such a formulation is dissolved in a separately prepared solution containing other components such as a surfactant, to obtain a liquid composition.

Now, practical formulation Examples of the liquid composition of the present invention will be described.

The reference numerals used in these Examples have the following meanings:

*1: Nonionic surfactant (polyoxyethyleneoctylphenyl ether), manufactured by Nippon Oil & Fats Co., Ltd.
*2: Anionic surfactant (sodium α-olefinsulfonate), manufactured by Nikko Chemical Co., Ltd.
*3: Viscosity builder (isobdtylene-maleic anhydride copolymer), manufactured by Kuraray Co., Ltd.
*4: Dilute hydrochloric acid as disclosed in the Guide Book for 11th Revised Edition of Japan Pharmacopoeia (containing from 9.5 to 10.5% (W/V) of hydrogen chloride), manufactured by Tokai Pharmaceutical Co., Ltd.
*5: Protease derived from bacteria, manufactured by Novo Nordisk Bioindustry Ltd.
*6: Protease derived from bacteria, manufactured by Novo Nordisk Bioindustry Ltd.
*7: Anionic surfactant (sodium lauroylmethylalanine), manufactured by Nikko Chemicals Co., Ltd.

(I) One-pack type

| | |
|---|---|
| (A) Nonion HS-220*1 | 2.0 g |
| OS-14*2 | 1.0 g |
| Isoban 110*3 | 0.5 g |
| Sodium chloride | 1.0 g |
| Borax | 0.5 g |
| Trisodium citrate decahydrate | 0.2 g |
| $CaCl_2.2H_2O$ | 0.01 g |
| Ethyl p-oxybenzoate | 0.002 g |
| (B) Glycerol | 10.0 g |
| Triethanolamine | 0.5 g |
| Dilute hydrochloric acid according to Pharmacopoeia*4 | 0.54 g |
| Esperase 8.0L*5 | 0.5 g |

The above components (A) are dissolved in 50 ml of purified water, then the above components (B) are added thereto, and the volume is adjusted to 100 ml with purified water.

(II) Two-pack type

| | |
|---|---|
| (A) Sodium chloride | 10.0 g |
| $CaCl_2.2H_2O$ | 0.1 g |
| Ethyl p-oxybenzoate | 0.02 g |
| Triethanolamine | 0.5 g |
| Dilute hydrochloric acid according to Pharmacopoeia | 0.54 g |

The above components are dissolved in 30 ml of purified water, then 75 g of glycerol and 5.0 g of Esperase 8.0L are added thereto, and the volume is adjusted to 100 ml with purified water to obtain a first solution.

| | |
|---|---|
| (B) Nonion HS-220 | 2.0 g |
| OS-14 | 1.0 g |
| Isoban 110 | 0.5 g |
| Glycerol | 2.5 g |
| Ethyl p-oxybenzoate | 0.002 g |
| Triethanolamine | 0.5 g |
| Dilute hydrochloric acid according to Pharmacopoeia | 0.54 g |

The above components are dissolved in 50 ml of purified water, and then the volume is adjusted to 100 ml with purified water to obtain a second solution.

In use, the first and second solutions are mixed in a ratio of 1:9 (by volume).

(III) Powder and solution type

| | |
|---|---|
| (A) Subtilisin A*6 | 0.25 g |
| Sodium chloride | 1.0 g |
| Sorbitol | 3.0 g |
| $CaCl_2.2H_2O$ | 0.01 g |
| Sodium nitrilotriacetate | 0.02 g |

The above components are preliminarily pulverized and stirred and mixed by a mixing machine to obtain a powder formulation.

| (B) Nonion HS-220*[7] | 2.0 g |
|---|---|
| Alaninate LN30*[7] | 1.0 g |
| Isoban 110 | 0.5 g |
| Glycerol | 5.0 g |
| Sorbitol | 7.0 g |
| Ethyl p-oxybenzoate | 0.02 g |
| Triethanolamine | 0.5 g |
| Dilute hydrochloric acid according to Pharmacopoeia | 0.54 g |

The above components are dissolved in 50 ml of purified water, and then the volume is adjusted to 100 ml with purified water to obtain a dissolving solution.

In use, the entire amount of the powder formulation is dissolved in the entire amount of the dissolving solution.

Thus, even when the liquid composition of the present invention is supplied in the form of a two-pack type or a solid type, once it is mixed, it can be used for cleaning and preserving contact lenses in the form of a single solution, whereby the user can easily perform the maintenance of contact lenses.

Namely, firstly, the contact lenses taken off from the eyes are brought in contact with the liquid composition of the present invention by soaking them in the liquid composition of the present invention or by dropping the liquid composition to the contact lenses, to remove the soils deposited on the lens surface by the action of the protease or the surfactant contained in the liquid composition. For adequate cleaning effects, the lenses are usually maintained in such a contact state at a temperature of from 5° to 40° C. for from one minute to 48 hours. Thereafter, the lenses may be rinsed with running water. In some cases, the liquid composition of the present invention is dropped to the lenses, followed by rubbing with fingers for cleaning before rinsing.

Further, in a case where a substantial amount of soil is deposited on the contact lenses, it is preferred to maintain the lenses in the contact state at a temperature of from 30° to 40° C. for from 1 to 48 hours. Because, the optimum temperature for the protease is usually at least 30° C. Further, the cleaning effects of a surfactant is usually high at a high temperature. However, at a temperature exceeding 40° C., there is a possible adverse effect to the lens material of the contact lenses.

Then, after completion of such a cleaning operation, the lenses may simply be soaked in the same liquid composition for their preservation.

Contact lenses may generally be classified into those made of hydrophilic material and those made of hydrophobic material. The liquid composition for contact lenses according to the present invention may be used for both types of contact lenses, and it is useful particularly for hydrophobic contact lenses. Specific examples of such hydrophobic contact lenses include those made essentially of polymethyl methacrylate or silicone rubber and those made of an oxygen permeable copolymer of polysiloxanylalkyl methacrylate with methyl methacrylate.

Now, the present invention will be described in further detail with reference to some Examples. However, it should be understood that the present invention is by no means restricted by such specific Examples.

Further, it should be understood that the present invention include various changes, modifications and improvements which can be made by those skilled in the art without departing from the spirit of the present invention, in addition to the following Examples and the specific embodiments described above.

EXAMPLE 1

Firstly, the respective components are added and dissolved in purified water in the proportions as identified in the following Table 1 to prepare various types of Sample Nos. 1 to 21. The substances identified by reference symbols a) to d) in Table 1 are all commercial products as identified below:

a: Protease derived from Actinomycetes, manufactured by Kaken Pharmaceutical Co., Ltd.
b: Protease derived from mold, manufactured by Amano Pharmaceutical Co., Ltd.
c: Nonionic surfactant (oxyethylene-oxypropylene-block polymer), manufactured by Nippon Oil and Fats Co., Ltd.
d: Viscosity builder (carboxymethyl cellulose), manufactured by Dycel Chemical Industries, Ltd.

TABLE 1

| Sample No. | | | 1 | 2 | 3 | 4 | 5 | 6 | 7 | 8 | 9 | 10 | 11 | 12 | 13 |
|---|---|---|---|---|---|---|---|---|---|---|---|---|---|---|---|
| Blend properties (%) (W/V) | Protease | Esperase 8.0L | 0.05 | 0.5 | — | — | — | — | — | — | — | 0.5 | 0.5 | 0.5 | 0.5 |
| | | Actinase AS[a] | — | — | 0.5 | 2 | — | — | — | — | — | — | — | — | — |
| | | Protease P(Amano)[b] | — | — | — | — | 0.5 | 5 | — | — | — | — | — | — | — |
| | | Subtilisin A | — | — | — | — | — | — | 0.05 | 0.25 | 1 | — | — | — | — |
| | Glycerol | | 5 | 10 | 20 | 30 | — | — | — | 5 | 5 | 10 | 10 | 10 | 10 |
| | Sorbitol | | — | — | — | — | 10 | 30 | 5 | 10 | 20 | — | — | — | — |
| | Sodium chloride | | 5 | 1 | 2 | 5 | 5 | 2 | 1 | 1 | 1 | 1 | 1 | 1 | 1 |
| | Surfactant | Nonion HS-220 | 8 | 2 | — | — | — | — | 0.5 | 2 | 8 | 2 | 2 | 2 | 2 |
| | | Pronon 204[c] | — | — | 8 | — | — | 8 | — | — | — | — | — | — | — |
| | | OS-14 | 2 | 1 | — | 1 | — | — | — | — | — | 1 | 1 | 1 | 1 |
| | | Alaninate LN30 | — | — | — | — | 1 | 2 | — | 1 | 2 | — | — | — | — |
| | CaCl$_2$.2H$_2$O | | 0.001 | 0.01 | 0.05 | 0.1 | — | — | 0.005 | 0.01 | 0.01 | 0.01 | 0.01 | 0.01 | 0.01 |
| | Triethanolamine | | 0.5 | 0.5 | 0.5 | 0.5 | 0.5 | 0.5 | 0.5 | 0.5 | 0.5 | 0.5 | 0.5 | 0.5 | 0.5 |
| | Pharmacopeial dilute hydrochloric acid | | 0.54 | 0.54 | 0.54 | 0.54 | 0.54 | 0.54 | 0.54 | 0.54 | 0.54 | 0.54 | 0.54 | 0.54 | 0.54 |
| | Ethyl p-oxybenzoate | | 0.02 | 0.02 | 0.02 | 0.02 | 0.02 | 0.02 | 0.02 | 0.02 | 0.02 | 0.02 | 0.02 | 0.02 | 0.02 |
| | Isoban 110 | | — | 0.5 | — | 0.5 | — | 0.5 | — | 0.5 | — | 0.5 | 0.5 | 0.5 | 0.5 |
| | Earnest gum FDM[d] | | 0.25 | — | 0.25 | — | 0.25 | — | 0.25 | — | 0.25 | — | — | — | — |
| | Trisodium citrate 10H$_2$O | | — | — | — | — | — | — | — | — | — | 0.2 | 2 | — | — |
| | Trisodium nitrilotriacetate | | — | — | — | — | — | — | — | — | — | — | — | 0.005 | 0.02 |
| | Borax | | — | — | — | — | — | — | — | — | — | — | — | — | — |

TABLE 1-continued

| Sample No. | | | 14 | 15 | 16 | 17 | 18 | 19 | 20 | 21 |
|---|---|---|---|---|---|---|---|---|---|---|
| Blend proper-ties (%) (W/V) | Protease | Esperase 8.0L | — | 0.5 | 0.5 | 0.5 | — | — | — | — |
| | | Actinase AS[a] | — | — | — | — | 0.5 | — | — | — |
| | | Protease P(Amano)[b] | — | — | — | — | — | 0.5 | — | — |
| | | Subtilisin A | 0.25 | — | — | — | — | — | 0.25 | 0.25 |
| | Glycerol | | 5 | 10 | 10 | 10 | 20 | — | 5 | 5 |
| | Sorbitol | | 10 | — | — | — | — | 10 | 10 | 10 |
| | Sodium chloride | | 1 | 1 | 1 | 1 | 2 | 5 | 1 | 1 |
| | Surfactant | Nonion HS-220 | 2 | 2 | 2 | 2 | — | — | 2 | 2 |
| | | Pronon 204[c] | — | — | — | — | 0.5 | 2 | — | — |
| | | OS-14 | — | 1 | 1 | 1 | — | — | — | — |
| | | Alaninate LN30 | 2 | — | — | — | — | 1 | 1 | 1 |
| | CaCl$_2$.2H$_2$O | | 0.01 | 0.01 | 0.01 | 0.01 | 0.05 | — | 0.01 | 0.01 |
| | Triethanolamine | | 0.5 | 0.1 | 0.8 | 0.8 | 0.8 | 0.6 | 0.6 | 0.6 |
| | Pharmacopeial dilute hydrochloric acid | | 0.54 | 0 | 0 | 0 | 0 | 0 | 0 | 0 |
| | Ethyl p-oxybenzoate | | 0.02 | 0.02 | 0.02 | 0.02 | 0.02 | 0.02 | 0.02 | 0.02 |
| | Isoban 110 | | 0.5 | 0.5 | 0.5 | 0.5 | — | — | 0.5 | 0.5 |
| | Earnest gum FDM[d] | | — | — | — | — | 0.25 | 0.25 | — | — |
| | Trisodium citrate 10H$_2$O | | — | — | — | 0.2 | — | — | — | — |
| | Trisodium nitrilotriacetate | | 0.02 | — | — | — | — | — | — | 0.02 |
| | Borax | | — | 0.05 | 0.5 | 0.5 | 0.5 | 0.3 | 0.3 | 0.3 |

The pH of each sample thus obtained was measured by means of the pH meter F-8E model, manufactured by Kabushiki Kaisha Horiba Seisakusho. With respect to each sample, the amount of the enzyme was measured immediately after the preparation and after the storage for 2 weeks at a temperature of 30° C., and the remaining activity (%) was calculated in accordance with the following formula. The results are shown in the following Table 2.

Remaining enzymatic activity (%) =

$$\frac{\text{Amount of enzyme after 2 weeks at 30° C.}}{\text{Amount of enzyme immediately after preparation}} \times 100$$

The amount of the enzyme was measured in the following manner. Namely, 2 ml of a sample diluted with a 1% sodium hydrogensulfite solution and 3 ml of a 1% sodium hydrogensulfite solution were put in a test tube and held in a constant temperature tank of 50° C. for 2 minutes to bring the solution to the constant temperature. Then, 2 ml of a 0.4% dimethylcasein solution (solvent: 0.34M boric acid buffer solution, pH 8.0) preliminarily heated to 50° C., was added thereto to initiate the enzymatic reaction, and 30 seconds later, 0.5 ml of a 0.1% sodium 2,4,6-trinitrobenzene sulfonate aqueous solution was added thereto. Then, after expiration of 25 minutes, 5 ml of ice water was added and left to stand at room temperature. Upon expiration of further 25 minutes, light of 425 nm was irradiated to measure the absorbance. The measured absorbance was compared with the preliminarily prepared calibration curve (the curve prepared by plotting the absorbance relative to the amount of the enzyme) to determine the amount of the enzyme.

TABLE 2

| Sample No. | pH | Remaining activity (%) |
|---|---|---|
| 1 | 7.89 | 90 |
| 2 | 7.86 | 88 |
| 3 | 7.81 | 87 |
| 4 | 7.76 | 97 |
| 5 | 7.71 | 55 |
| 6 | 7.10 | 58 |

TABLE 2-continued

| Sample No. | pH | Remaining activity (%) |
|---|---|---|
| 7 | 7.83 | 88 |
| 8 | 7.89 | 93 |
| 9 | 7.88 | 71 |
| 10 | 7.87 | 86 |
| 11 | 7.84 | 88 |
| 12 | 7.84 | 85 |
| 13 | 7.86 | 90 |
| 14 | 7.85 | 71 |
| 15 | 7.69 | 99 |
| 16 | 7.79 | 100 |
| 17 | 7.79 | 100 |
| 18 | 7.72 | 100 |
| 19 | 7.59 | 70 |
| 20 | 7.63 | 98 |
| 21 | 7.58 | 99 |

COMPARATIVE EXAMPLE 1

Firstly, eight types of comparative samples were prepared by diluting commercially available proteases to the proportions as identified in the following Table 3. As the diluting solution, either a 0.5% triethanolaminehydrochloric acid buffer solution (pH 7.8) or a commercially available cleaning-preserving solution for oxygen permeable hard contact lenses, O$_2$ CARE (tradename, manufactured by Menicon Co., Ltd.) was used. The amount of the enzyme was measured immediately after the preparation and after the storage for 5 days at a temperature of 30° C., in the same manner as in Example 1, and the remaining activity was calculated. The results are shown also in Table 3.

TABLE 3

| | Enzyme | | | Remaining activity (%) |
|---|---|---|---|---|
| No. | Type | Proportion % (W/V) | Diluent | |
| 1 | Esperase 8.0L | 0.5 | Buffer solution | 4 |
| 2 | | 0.5 | O$_2$ CARE | 0 |
| 3 | Actinase AS | 0.5 | Buffer solution | 5 |

TABLE 3-continued

| No. | Enzyme Type | Proportion % (W/V) | Diluent | Remaining activity (%) |
|---|---|---|---|---|
| 4 | | 0.5 | O$_2$ CARE | 3 |
| 5 | Protease P | 0.5 | Buffer solution | 2 |
| 6 | (Amano) | 0.5 | O$_2$ CARE | 1 |
| 7 | Subtilisin A | 0.25 | Buffer solution | 5 |
| 8 | | 0.25 | O$_2$ CARE | 3 |

As is evident from the comparison between Example 1 and Comparative Example 1, all the samples prepared in accordance with the present invention have remarkably high remaining activities. Further, from the comparison between Sample No. 2 and Sample Nos. 15 and 16, between No. 10 and No. 17, between No. 3 and No. 18, between No. 5 and No. 19, between No. 8 and No. 20 and between No. 14 and No. 21 in Example 1, it is observed that by an addition of borax, the stability of the enzyme is further improved.

EXAMPLE 2

To examine the cleaning effects of the liquid compositions of the present invention, lenses artificially soiled by artificial tear and lipids were prepared, and cleaning tests were conducted by using Sample Nos. 2, 3, 5 and 8 prepared in Example 1.

Preparation of Artificially Soiled Lenses

Firstly, the following components were dissolved in 80 ml of purified water, thin the pH was adjusted to 7.4 with 1N sodium hydroxide. Further, the volume was adjusted to 300 ml with purified water to obtain an artificial tear.

| Composition of artificial tear | |
|---|---|
| Bovine serum albumin | 0.394 g |
| Bovine serum γ-globulins | 0.275 g |
| Egg-white lysozyme | 0.129 g |
| Sodium chloride | 0.830 g |
| Calcium chloride (dihydrate) | 0.022 g |
| Sodium dihydrogenphosphate (dihydrate) | 0.080 g |
| Swine gastric mucin | 0.150 g |

Then, in 1.5 ml of this artificial tear, a highly oxygen-permeable hard contact lens (Menicon EX, manufactured by Menicon Co., Ltd.) was soaked and heated at 75° C. for 30 minutes and then cooled. To such a lens, a commercially available cleaning-preserving solution (O$_2$ CARE, manufactured by Menicon Co., Ltd.) was dropped, and the soil deposited on the surface was removed as far as possible by rubbing the lens with fingers. This operation was repeated six times.

After such operations, the lens was observed under 20 magnifications by a dark-field microscope (manufactured by Olympus Optix Co., Ltd.), whereby it was observed that white soil was deposited over the entire lens.

Further, this lens was soaked in a solution prepared by dissolving 0.1 g of beef tallow and 0.1 of olive oil in 100 ml of physiological saline of 50° C. and stirred for 5 minutes by a magnetic stirrer. Then, it was taken out to obtain an artificially soiled lens. By the microscopic observation in the same manner as above, it was found that oil in the form of white soil was deposited on this artificially soiled lens.

Cleaning Test

Into a vial, 1.5 ml of a solution of Sample 2 prepared in Example 1 was put, and the above artificially soiled lens was soaked therein and left to stand at 20° C. for 4 hours. Then, the lens was taken out, and gently washed with the same sample solution by fingers and then rinsed with running water. Thereafter, it was observed under 20 magnifications by the dark-field microscope, whereby it was observed that white soil and oil were completely removed from the lens.

Such a cleaning test was conducted by using the solutions of Sample Nos. 3, 5 and 8 prepared in Example 1, respectively, whereby it was observed that soils were likewise completely removed from the lenses.

COMPARATIVE EXAMPLE 2

Using a commercially available cleaning solution for oxygen permeable hard contact lenses (O$_2$ CARE, manufactured by Menicon Co., Ltd.), the cleaning of an artificially soiled lens was conducted in the same manner as in Example 2. Thereafter, the microscopic observation was conducted, whereby it was observed that only the oil soil was removed, and no substantial removal of white deposition was observed.

COMPARATIVE EXAMPLE 3

Comparative samples were prepared in the same manner as in Example 1 with respect to the solutions of Samples Nos. 2, 3, 5 and 8 prepared in Example 1, except that the concentration of glycerol was changed to 50% (W/V).

Using these comparative samples respectively, the cleaning of artificially soiled lenses were conducted in the same manner as in Example 2. Thereafter, the microscopic observation was conducted, whereby in each lens, the major proportion of soil was not removed although white deposition was slightly removed.

EXAMPLE 3

Using the solutions of Sample Nos. 2, 3, 5 and 8 prepared in Example 1 respectively, cleaning of highly oxygen permeable hard contact lenses (Menicon EX, manufactured by Menicon Co., Ltd.) which were used for 6 months, was conducted in the same manner as in Example 2.

As a result, after the cleaning operation, it was observed that the soil was completely removed from each lens, although prior to the cleaning, deposition of white soil was observed on each lens.

EXAMPLE 4

The solutions of Sample Nos. 2, 3, 5 and 8 prepared in Example 1 were stored at a temperature of 30° C. for 2 weeks. Using such samples, cleaning of artificially soiled lenses was conducted in the same manner as in Example 2.

As a result, the soil of each lens was completely removed by each of the samples, and the effects of substantially the same level as immediately after the preparation of the samples were observed.

EXAMPLE 5

The solutions of Sample Nos. 2, 3, 5 and 8 prepared in Example 1 were stored at a temperature of 30° C. for 2 weeks. Using such samples, cleaning of highly oxygen permeable hard contact lenses (Menicon EX, manufactured by Menicon Co., Ltd.) which were used for 6 months, was conducted in the same manner as in Example 2.

As a result, the soil of each lens was completely removed by each of the samples, and the effects of substantially the same level as immediately after the preparation of the samples were observed.

EXAMPLE 6

Using the solutions of Sample Nos. 2, 10, 13, 16 and 17 prepared in Example 1 respectively, cleaning of artificially soiled lenses was conducted in the same manner as in Example 2 except that the soaking time was varied to 0.5 hour, 1 hour, 2 hours, 4 hours and 6 hours.

As a result, by each of the samples, the soil was removed within 6 hours. The cleaning speed was highest with Sample Nos. 1 and 13, and then in the order of the solutions of Sample Nos. 2, 17 and 16. Namely, it has been found that the cleaning effects are higher when trisodium citrate decahydrate or trisodium nitrilotriacetate is incorporated. Further, it was observed that the cleaning effects were slightly low when borax was incorporated.

As is apparent from the foregoing description, the liquid composition for contact lenses according to the present invention has a feature that the incorporated protease and surfactant effectively remove the soils of contact lenses and yet the effects for removing the soils can be maintained for a long period of time by the stabilization of the protease. Therefore, in use, the contact lenses may simply be brought in contact or soaked in the liquid composition, and cleaning of contact lenses can be conducted very simply without necessity of dissolving or diluting the composition, and the composition of the present invention is also useful as a preserving solution.

We claim:

1. A method for cleaning and preserving a contact lens, which comprises soaking the contact lens in a liquid composition comprising from 0.01 to 5% (W/V) of a protease, from 5 to 30% (W/V) of a polyhydric alcohol, from 1 to 5% (W/V) of an alkali metal salt, from 0.5 to 20% (W/V) of a surfactant, and from about 0.05% (W/V) of a borate, thereby stabilizing enzymatic activity of the protease for an extended period of time without diluting the liquid composition, so that the contact lens is cleaned while being preserved.

2. The method of claim 1, wherein said liquid composition further contains not more than 2% (W/V) of nitrilotriacetic acid or a salt thereof or an α-carboxylic acid or a salt thereof.

3. The method of claim 1, wherein in said liquid composition, the protease is a serine protease.

4. The method of claim 1, wherein in said liquid composition, the polyhydric alcohol is at least one member selected from the group consisting of glycerol, sorbitol, mannitol, erythritol, dulcitol and inositol.

5. The method of claim 1, wherein in said liquid composition, the alkali metal salt is selected from the group consisting of a sodium salt, a potassium salt and a lithium salt.

6. The method of claim 5, wherein said alkali metal salt is selected from the group consisting of sodium chloride, potassium chloride and lithium chloride.

7. The method of claim 1, wherein said borate is an alkali metal borate.

8. The method of claim 1, wherein the surfactant is selected from the group consisting of a non-ionic surfactant and an anionic surfactant.

9. The method of claim 8, wherein said non-ionic surfactant is selected from the group consisting of a polyalkylene glycol adduct of a higher alkylamine, a polyethylene glycol adduct of a higher fatty acid amide, a polyglycerol ester of a higher fatty acid, a polyalkylene glycol of a higher fatty acid, a polyethylene glycol copolymer ester, a polyethylene glycol ether of a higher alcohol, a polyglycerol ether of a higher alcohol, a formaldehyde condensation product of polyethylene glycol of an alkylphenol, a polypropylene glycol-polyethylene glycol copolymer and a polyethylene sorbitan alkyl ester.

10. The method of claim 8, wherein said anionic surfactant is selected from the group consisting of sodium alkylsulfate, sodium alkylbenzene sulfonate, sodium alkyloylmethyl taurine, sodium alkyloylsarcosine, sodium α-olefinsulfonate, sodium polyethylene alkyl ether sulfate and sodium polyoxyethylenealkylphenol ether sulfate.

11. The method of claim 8, wherein said non-ionic surfactant and said anionic surfactant are used in a ratio of about 100:0 to 20:80 (W/W).

12. The method of claim 1, wherein said liquid composition further comprises calcium ions in an amount of not greater than about 0.01% (W/V).

13. The method of claim 12, wherein said calcium ions are supplied from a source selected from the group consisting of calcium chloride, calcium nitrate and calcium acetate.

* * * * *